United States Patent [19]

Godfrey

[11] Patent Number: 4,992,385

[45] Date of Patent: Feb. 12, 1991

[54] POLYMER-COATED OPTICAL STRUCTURES AND METHODS OF MAKING AND USING THE SAME

[75] Inventor: Robin E. Godfrey, Welwyn, United Kingdom

[73] Assignee: Ares-Serono Research and Development Limited Partnership, Boston, Mass.

[21] Appl. No.: 76,519

[22] Filed: Jul. 22, 1987

[30] Foreign Application Priority Data

Jul. 24, 1986 [GB] United Kingdom ............... 8618133

[51] Int. Cl.⁵ ..................................... G01N 33/553
[52] U.S. Cl. .................................. 436/525; 264/212; 264/298; 350/96.19; 422/57; 422/56; 422/69; 422/82.11; 427/162; 427/409; 427/435; 436/528; 436/805
[58] Field of Search .............. 436/805, 525, 164, 807, 436/528; 250/461.1, 461.2; 422/55-57, 58, 69, 82.11; 350/96.19; 264/212, 298; 427/169, 430.1, 162, 409, 410, 435

[56] References Cited

U.S. PATENT DOCUMENTS

| | | | |
|---|---|---|---|
| 3,839,067 | 10/1974 | Sosnowski et al. | 350/96.19 X |
| 3,926,564 | 12/1975 | Giaever | 23/253 TP |
| 3,979,184 | 9/1976 | Giaever | 23/253 TP |
| 4,080,476 | 3/1978 | Laskey | 428/413 |
| 4,357,142 | 11/1982 | Schall | 436/531 |
| 4,363,634 | 12/1982 | Schall | 436/531 |
| 4,521,522 | 6/1985 | Lundstrom et al. | 436/525 |
| 4,537,861 | 8/1985 | Elings | 436/805 X |
| 4,586,980 | 5/1986 | Hirai et al. | 156/655 |
| 4,637,684 | 1/1987 | Tomita et al. | 350/96.19 |
| 4,647,544 | 3/1987 | Nicoli | 436/805 X |
| 4,815,843 | 3/1989 | Tiefenthaler et al. | 356/128 |
| 4,877,747 | 10/1989 | Stewart | 422/68 X |

FOREIGN PATENT DOCUMENTS

| | | |
|---|---|---|
| 112721 | 7/1984 | European Pat. Off. . |
| 178083 | 4/1986 | European Pat. Off. . |
| 202021 | 11/1986 | European Pat. Off. . |
| 1108461 | 7/1961 | Fed. Rep. of Germany . |
| 3343636 | 6/1984 | Fed. Rep. of Germany . |
| 3346795 | 7/1985 | Fed. Rep. of Germany . |
| WO86/901 | 3/1986 | PCT Int'l Appl. . |
| 271200 | 1/1951 | Switzerland . |
| WO85/05317 | 12/1985 | World Int. Prop. O. . |
| WO86/07149 | 12/1986 | World Int. Prop. O. . |

OTHER PUBLICATIONS

IBM Technical Disclosure Bulletin, vol. 25, No. 10, pp. 4976-4977 (Mar. 1983).
Horejsi et al., J. Immunol. Methods, 62:325 (1983).
Liedberg et al., Sensors and Actuators, 4:299 (1983).
Sugi, J. Mol. Electronics, 1:3 (1985).
Fukuda et al., J. Colloid and Interface Science, 54:430 (1976).

*Primary Examiner*—Robert J. Hill, Jr.
*Attorney, Agent, or Firm*—Stephan P. Williams

[57] ABSTRACT

A method of treating the surface of an optical structure which comprises forming on the surface a thin layer of organic polymer using a solvent casting technique. Preferably the process includes the subsequent treatment of the polymer layer with a solution of a specific ligand.

Complex formation between the bound ligand and its specific binding partner present in a sample to be analyzed alters the optical properties of the diffraction grating surface and the change can form the basis of an assay method.

20 Claims, No Drawings

POLYMER-COATED OPTICAL STRUCTURES AND METHODS OF MAKING AND USING THE SAME

The present invention relates to methods of producing polymer-coated surfaces suitable for use as optical structures. In particular it relates to methods of producing surfaces suitable for use in sensors, for example in biosensors in which one of a pair of binding partners is applied to the surface of a polymer-coated optical structure to form a device for detecting the presence of the complementary component in a sample subsequently brought into contact with the surface.

The properties of simple optical structures have been known for many years and structures such as, for example, diffraction gratings have widespread use, not only as tools for understanding and analysing the wave properties of electromagnetic radiation but also, more recently, as sensors for detecting chemical, biochemical or biological species in a sample.

U.S. Pat. Nos. 3,926,564 and 3,979,184 both describe the adsorption of immunologically reactive proteins onto rough metallic surfaces such that binding of a complementary component changes the optical properties of the surface in a manner detectable by the unaided eye.

EP-0112721 describes the preparation, and use as biosensors, of diffraction gratings coated with a material (hereinafter called "specific binding partner") capable of binding with the species to be assayed (hereinafter called "ligand") to form a complex. The optical properties of such diffraction gratings are altered as a result of complex formation between the specific binding partner and the ligand and this phenomenon can consequently form the basis of an assay system.

A problem common not only to the use of coated optical structures as biosensors but also to the use of standard optical structures by experimental physicists, is the difficulty of controlling their surface properties. The supporting substrate of such optical structures is often of glass or plastics material but the surface of the structure may comprise a thin metal layer formed, for example, by vacuum deposition. Problems can arise with the use of metal-coated surfaces in corrosive environments which may destroy the integrity of a metal layer. Other inorganic layers e.g. silicon oxide have also been described as diffraction grating surfaces (see, for example, EP-0112721 and EP-0178083). Certain of the optical properties of an optical structure, for example its reflection and/or transmission properties and any surface plasmon resonance effect exhibited, will depend on the composition, thickness and uniformity of such surface layers; the composition of the surface layer also governs its chemical properties. However, the range of chemical and physical properties of known inorganic layers is limited. A still further problem which may occur when using such optical structures as biosensors is that some biologically active molecules, e.g. proteins, may be at least partially inactivated by direct contact with metallic and certain inorganic surfaces.

In contrast, an extremely wide range of chemical and physical properties can be achieved by using appropriate organic polymers and a large number of techniques are known for bonding thereto or adsorbing thereon chemical, biochemical and biological entities. Unfortunately, previous attempts to prepare polymer-coated diffraction gratings have resulted in the polymer coating failing to conform adequately to the surface relief profile of the grating thereby grossly distorting its inherent physical properties.

We have now found that by employing a particular technique known as "solvent casting" it is possible to prepare an optical structure having a uniformly distributed surface layer of organic polymer which conforms well to the surface relief profile of the optical structure.

Thus, in its broadest aspect, the invention provides a method of treating the surface of an optical structure which comprises forming on said surface a thin layer of organic polymer using a solvent casting technique.

In general, the layer of polymer applied to the surface of the grating will have a thickness in the range of 5 nanometers to 100 nanometers, preferably 15 to 20 nanometers. The polymer may be any suitable material which can be cast in a thin layer using a solvent casting technique. The use of cellulose derivatives such as, for example, cellulose nitrate, as the polymer layer is particularly preferred but other polymers may also be used, for example, those mentioned hereinafter.

As mentioned previously the optical characteristics of an optical surface depend not only on its physical relief profile but also on the composition of the surface layer or layers. Thus, the process of the present invention can be applied to produce novel coated optical structures which may prove to be useful tools for experimental physicists and the like. In addition, certain preferred surface layers such as, for example, those capable of supporting surface plasmon resonance e.g. silver may be susceptible to corrosion by, for example, aqueous environments; the present invention provides a means of passivating such a layer such that its integrity is maintained under practical working conditions.

However, the present invention is of particular advantage where the optical structures are diffraction gratings intended to be used as biosensors in a manner analogous to previous proposals (see, for example, EP-0112721). Direct contact between a biologically active material, such as, for example, an antibody or antigen, and a metallic surface may result in contamination or destruction of its biological activity. In this situation the polymer layer conveniently acts as a barrier. Furthermore, the wide range of chemical properties of different polymer surfaces (e.g. availability of free groups for covalent bonding, hydrophilicity or hydrophobicity, surface charge and dielectric properties) provide versatility and scope for optimising the binding or adsorption of any particular binding partner, such as, for example, an antibody or an antigen. It is important to maintain the native conformation and biological activity of the desired binding partner and to obtain satisfactory immobilisation onto the surface of the optical structure while minimizing any non-specific binding or steric hindrance.

The method of the present invention hence has particular use in the preparation of biosensors and thus according to one embodiment of the present invention there is provided a method of preparing a device for the detection of a ligand which comprises applying to the surface of an optical structure a thin layer of an organic polymer by means of a solvent casting technique and adsorbing on or binding to the said organic polymer, either directly or indirectly, a specific binding partner for the ligand it is desired to detect.

Biosensors produced in accordance with the invention are especially useful for the detection of antibodies or antigens (in which case the specific binding partner will be an antigen or an antibody, monoclonal or polyclonal, respectively) but other ligands may be detected by the use of other specific binding partners, as discussed hereinafter. However, the sensors produced in accordance with the invention are not limited to biosensors and may comprise chemical sensors such as, for example, gaseous chemical detectors wherein specific adsorption onto or absorption into the polymer layer may occur.

The optical properties of an optical structure coated with a specific binding partner are altered by complex formation between the specific binding partner and the complementary ligand and, in one embodiment of the invention, by comparing the optical characteristics of a standard (untreated) region with those of a treated test region of the surface it is possible to determine qualitatively whether a binding reaction has occurred in the test region. In an alternative embodiment where, for example, the specific binding partner is an antibody, an antibody specific to the antigen to be tested for is adsorbed on or bound to at least one discrete test region on the surface of an optical structure and a protein which is not a specific binding partner for any ligand which may be present in the sample to be tested (denoted herein as a "non-specific protein") is adsorbed on or bound to at least one discrete reference region on said surface. The non-specific protein may be, for example, an inactivated antibody or an antibody raised against a ligand not present in the samples to be tested e.g. where the samples to be tested are human sera, the non-specific protein may be an anti-mouse antibody. Any differences between the non-specific binding of e.g. proteins present in the test sample to either the specific antibody or the non-specific protein can be determined by comparing the optical properties of the test region with the reference region after exposure to a sample which does not contain the antigen to be tested for, so that an appropriate correction can, if necessary, be made. Comparison of the optical characteristics of the test and standard regions of a similar biosensor during or after exposure to a sample to be tested can then provide a measurement of complex formation between the antigen to be tested for and its specific antibody. Each region may comprise a continuous layer of a specific binding partner or each binding partner may be present at discrete intervals within any given region to form a discontinuous layer.

The biosensors produced in accordance with the invention may, for example, be used in assays in ways analogous to those described in EP-0112721 and EP-0178083.

Thus according to a further feature of the present invention there is provided a method of detecting a ligand in a sample which comprises contacting said sample with a biosensor prepared by the process hereinbefore defined and determining whether, and if desired the extent to which and/or rate at which, an optical characteristic of the biosensor is altered by formation of a complex between the ligand and the specific binding partner.

The present invention further provides a biosensor for detecting a ligand comprising an optical structure bearing a thin layer of an organic polymer, which has been applied to the surface of the optical structure by a solvent casting technique, the said organic polymer having adsorbed thereon or bound thereto, either directly or indirectly, a specific binding partner for the ligand it is desired to detect.

Solvent casting of polymers onto solid or liquid surfaces is a well known technique, reviewed by Mano and Durao, Journal of Chemical Education (1973), 50, 228. The article entitled "On the Technique of Making Thin Celluloid Films" by James Taylor, published in the Journal of Scientific Instruments for 1925 to 1926, Volume 3, pages 400–404, describes the formation on a water surface of celluloid films having thicknesses of the order of 50 nm.

The solvent casting technique preferably used in accordance with the invention involves the formation of a thin polymer film on a liquid surface using a solvent, and subsequently causing relative movement between the surface of the optical structure on which the film is to be formed and the thin polymer film on the liquid surface such that they are brought into contact. The thickness of the film on the liquid surface will to a large extent determine the thickness of the film on the surface of the optical structure, and the thickness of the film on the liquid surface will itself be governed by the quantity and the nature of the polymer used, the surface area and nature of the casting liquid (the term "casting liquid" as used herein refers to the bulk liquid on the surface of which the polymer film is cast). Thus, for example, one drop from a capillary tube of a mixture of 3 g cellulose nitrate in 100 ml of amyl acetate can be made to spread out on a sufficiently large water surface to give a film of cellulose nitrate of only a few nanometers thickness.

As an alternative to solvent casting techniques involving a casting liquid, in certain circumstances it may be possible to cast the film directly onto the surface of the optical structure itself or onto another solid surface followed by transfer of the film to the surface of the optical structure.

The invention will now be described in more detail with reference to a preferred embodiment wherein the optical structure is a diffraction grating. However, it is to be understood that other optical structures such as, for example, optical waveguides, optical fibres and metal-coated prisms in the correct configuration to exhibit surface plasmon resonance, are all included within the scope of the invention.

As previously mentioned, the supporting substrate of a diffraction grating may comprise glass or plastics material; polycarbonate is particularly preferred. The diffraction grating may be formed in the surface of the supporting substrate which may be covered with, for example, a metal film, such as silver, gold, copper, nickel or aluminium, formed by a process of vapour deposition, electroplating, sputtering, coating, painting, spraying or otherwise. Preferably the metal surface is capable of supporting surface plasmon resonance, and more particularly is of silver, and the metallic film is deposited by vacuum deposition.

Where the diffraction grating is to be used in an optical transmission mode, the metal film must be sufficiently thin, for example up to 50 nm for silver, so as not to unduly impede the passage of light therethrough. Where the diffraction grating is to be used in a reflective mode, then the metal layer can be thicker, for example up to 500 nm, preferably around 100 nm for silver, and is preferably made sufficiently dense to provide a good reflecting surface on the diffraction grating pattern in the surface of the supporting substrate e.g. of plastics or glass.

A particularly preferred method of applying a polymer film to the surface of a metallized diffraction grating comprises the steps of:

1. inserting a metallised polycarbonate diffraction grating into a bath containing the casting liquid, preferably de-ionized distilled water,
2. forming a thin film of the desired polymer over the surface of the casting liquid, and
3. either raising the diffraction grating through the casting liquid to engage the film of polymer on the surface of the liquid or allowing the casting liquid to drain out of the bath so that the polymer film on the surface of the liquid drops as the liquid level drops until it engages and spreads over the surface of the metallized diffraction grating, in either case the diffraction grating being located at a small angle to the horizontal to facilitate draining of the casting liquid from the surface of the diffraction grating.

Where the diffraction grating is intended to be used as a biosensor as described above the solution of the specific binding partner is preferably left in contact with the polymer for a controlled period of time and, where appropriate, under controlled conditions of temperature, pressure, humidity and the like. The process will normally have to be performed under "clean room" conditions and, particularly where the binding partner is a biologically active substance, all the usual precautions must be taken for handling such materials in order to avoid contamination and denaturation or inactivation in any way.

Any surplus solution is preferably removed from the polymer surface and may be recovered by suction or washing and recycled or simply washed away as waste.

The final coated diffraction grating may be dried or otherwise treated and packaged, again generally under "clean room" conditions.

Techniques for bonding specific binding partners to solid phase supports are described in the literature. The binding partner may be bound to the polymer either directly or indirectly. Indirect binding may, for example, be effected by binding to the polymer a reagent Y which selectively interacts with a reagent Z provided on the specific binding partner. In such cases, the reagent Z may for example be such as to render the specific binding partner antigenic to reagent Y which in that case will be an antibody raised to Z. Z may for example be fluorescein isothiocyanate, rhodamine isothiocyanate, 2,4-dinitrofluorobenzene, phenyl isothiocyanate or dansyl chloride. Reagents Y and Z may alternatively be a specific binding protein and the corresponding ligand such as for example avidin and biotin.

It is a desirable but not an essential feature of the invention to provide covalent bonding of the binding partner to the polymer.

The bonding of the specific binding partner, either directly or indirectly, to the polymer may be facilitated by activating the polymer layer, to provide free reactive groups for bonding. Thus, for example, cellulose nitrate can be activated by cyanogen bromide in aqueous solution of preferred pH 10-11. Typically, the cellulose surface is left in contact with the cyanogen bromide solution for a controlled period of time, typically of the order of a few minutes, while pH is controlled within the limits indicated above. After this reaction the diffraction grating is removed from the cyanogen bromide solution and washed in cold distilled water and thereafter is optionally dried and stored pending the application thereto of a binding partner, such as, for example, an antibody or an antigenic protein.

The binding of a specific binding partner to an activated polymer surface may be conveniently effected by contacting a solution of the specific binding partner with the polymer surface such that, where the polymer has been activated by the provision of reactive groups as described above, the binding partner may attach to or associate with the reactive groups on the polymer surface. Typically droplets of the solution may be applied to the polymer surface and left for a controlled period of time (typically of the order of some hours) in a controlled environment (particularly a humidity-controlled environment to prevent drying) and in clean room conditions, so that a sufficient quantity of the binding partner becomes bound to the surface of the polymer.

However, the use of cyanogen bromide may not be appropriate if the material which is to be bonded to the polymer is other than a protein, such as, for example, an antigenic polysaccharide.

The invention has wide application and merely as one example may be used in the detection of the Group A Streptococcal bacteria or bacterial antigen in childhood illnesses. However, it is to be understood that the coated diffraction gratings and biosensor diagnostic testing devices produced by the invention are not in any way limited to such an application and can be used for any diagnostic test provided the appropriate binding partner has been applied to the surface of the diffraction grating.

The invention will be particularly described hereinafter with reference to an antibody or an antigen as the specific binding partner or ligand. However, the invention is not to be taken as being limited to methods of preparing biosensors suitable for use in antibody or antigen assays but includes within its scope any sensors prepared by the process of the invention which can be used to detect any chemical, biochemical or biological species in a sample. Examples of suitable binding partners which may be immobilized on an optical structure prepared by the process of the invention and of ligands which may be assayed by the method of the invention are given in Table I below.

TABLE I

| Ligand | Specific Binding Partner |
|---|---|
| antigen | specific antibody |
| antibody | antigen |
| hormone | hormone receptor |
| hormone receptor | hormone |
| polynucleotide strand | complementary polynucleotide strand |
| avidin | biotin |
| biotin | avidin |
| protein A | immunoglobulin |
| immunoglobulin | protein A |
| enzyme | enzyme cofactor (substrate) or inhibitor |
| enzyme cofactor (substrate) or inhibitor | enzyme |
| lectins | specific carbohydrate |
| specific carbohydrate of lectins | lectins |

The method of the invention has very broad applicability but in particular may be used to provide biosensors suitable for assaying: hormones, including peptides hormones (e.g. thyroid stimulating hormone (TSH), luteinising hormone (LH), human chorionic gonadotrophin (hCG), follicle stimulating hormone (FSH), insulin and prolactin) and non-peptide hormones (e.g. steroid hormones such as cortisol, estradiol, progesterone and testosterone, or thyroid hormones such as thyroxine (T4) and triiodothyronine), oroteins (e.g. carcinoembryonic antigen (CEA) and alphafetoprotein (AFP)), drugs (e.g. digoxin), sugars, toxins, vitamins, viruses, bacteria or microorganisms.

It will be understood that the term "antibody" used herein includes within its scope
(a) any of the various classes or sub-classes of immunoglobulin, e.g. IgG, IgM, derived from any of the animals conventionally used, e.g. sheep, rabbits, goats or mice,
(b) monoclonal antibodies,
(c) intact molecules or "fragments" of antibodies, monoclonal or polyclonal, the fragments being those which contain the binding region of the antibody, i.e. fragments devoid of the Fc portion (e.g., Fab, Fab', F(ab')$_2$) or the so-called "half-molecule" fragments obtained by reductive cleavage of the disulphide bonds connecting the heavy chain components in the intact antibody.

The method of preparation of fragments of antibodies is well known in the art and will not be described herein.

The term "antigen" as used herein will be understood to include both permanently antigenic species (for example, oroteins, bacteria, bacteria fragments, cells, cell fragments and viruses) and haptens which may be rendered antigenic under suitable conditions.

The following examples describe the preparation of cellulose nitrate films and their subsequent transfer onto diffraction gratings and the binding or adsorption of biological materials onto the surface of such polymer-coated gratings.

PREPARATION OF CELLULOSE NITRATE FILMS AND TRANSFER ONTO DIFFRACTION GRATING

All solutions and casting liquids used for the preparation of polymer films and their transfer onto diffraction gratings should be filtered to remove contaminating particles and all operations should be carried out in a clean room.

In a preferred method, a casting tank is chosen such that the area of the water surface is larger (by a factor of 5 or more) than the area of the grating to be covered. This ensures that the diffraction grating is not covered by an edge of the cast polymer film. Where a very thin layer of polymer is required the surface area of the casting tank is preferably sufficiently larger than the area of the cast film to avoid any "edge effect" e.g. five times larger. However, for thicker films it may be preferred to cast the polymer into a ring on the surface on the casting liquid, the area of which can be readily adjusted to control the thickness of the polymer layer.

The tank is cleaned, particularly to remove grease, surfactants or other contaminants, and a diffraction grating support is placed at the bottom of the tank. This support may, for example, comprise a wire grid located at a small angle to the horizontal to allow water to drain between the cast film and the diffraction grating as the two are brought into contact.

The tank is filled with distilled water. It may be advantageous but not essential to adjust the pH or ionic strength of this water in order to promote good adhesion of the polymer film to the diffraction grating. The water level must be above the surface of the diffraction gratings which are to rest on the support.

Diffraction gratings are placed on the support before or after addition of water, grating side up. The diffraction gratings should be clean and free of grease, surfactants or other contaminants before entering the casting tank.

Once the water surface has settled a drop of cellulose nitrate solution, for example cellulose nitrate in amyl acetate, is dropped onto the centre of the water surface. Provided the water surface is free of surfactants, the cellulose nitrate solution spreads to a well defined circular area and the liquid film dries within a few seconds. The rate of drying of the film may be controlled by covering the casting tank with a lid provided with a small hole in the centre through which the cellulose solution is applied. With a uniform film thickness, reflected light interference colours may be observed as the film dries successively thinner.

If the water surface is not clean, the thickness of the cellulose film formed is not uniform and it spreads out into a non-circular patch with 'fingers' extending outwards. The non-uniform film thickness is apparent from the random distribution of reflected interference colours.

A polymer film thickness of about 16 nanometers is produced by addition of 10 microliters of a 9% cellulose nitrate solution (9 g cellulose nitrate in 100 ml amyl acetate).

Once the film has dried, water is drained out through a tap at the bottom of the tank, such that the dried polymer film is lowered onto the diffraction grating surface. The diffraction grating and its support are gently removed from the tank and left to dry for several minutes.

We have found that the adhesion of cellulose nitrate to silver-coated polycarbonate diffraction gratings is enhanced by casting the polymer films onto distilled water whose pH has been adjusted to 9 by the addition of, for example, NaOH.

The use of any other solvent castable polymers is possible with the correct choice of solvents and casting surfaces. Thus, for example, cellulose acetate films may be cast from amyl acetate, polystyrene from xylene, polyisobutylene from petroleum ether and polyvinyl chloride—acetate copolymer films can be cast from cyclohexanone onto water surfaces. In some circumstances enforced spreading of the solution on the casting liquid, using conventional techniques, may be necessary.

Film thickness may be controlled by careful selection of:
polymer solution concentration
volume of material applied to the casting liquid surface
type of solvent.

Amyl acetate for example is amphiphilic and spreads rapidly over a clean water surface. Other solvents may not spread as rapidly, with concomitant increases in film thickness.

The technique is not limited to casting on a water surface and other liquids may be used for the casting surface provided the solvent used is largely immiscible with, and the polymer-containing solution is of lower density than, the casting liquid. Thus, for example, ethyl cellulose can be cast onto mercury, diisocyanates together with polyols can be co-cast onto mercury and gelatin can be cast from water onto carbon tetrachloride. It is also possible to produce thin polymer layers using the solvent casting technique to cast the polymer onto a solid surface. Thus, for example, polyethylene terephthalate can be cast from trifluoroacetic acid, polycarbonate from dichloromethane, polyvinyl formal from dioxan, polysulfone from chloroform, cellulose acetate from acetone and polypropylene can be cast from xylene, in each case on to an appropriate substrate. It is to be understood that where the polymer is cast onto a casting liquid the casting liquid must be compatible with the material of the diffraction grating immersed therein and where the polymer is cast onto a solid surface the solvent used to bring the polymer into solution prior to casting must be compatible with the material of the solid surface.

BINDING OF BIOLOGICAL MATERIALS TO THE POLYMER SURFACE

Three different methods of coupling biological molecules to a cellulose nitrate polymer surface on a diffraction grating, have been considered:
(a) covalent bonding
(b) non-covalent adsorption
(c) covalent bonding of the biological molecule to a polymer which is entrapped within the cellulose nitrate.

(a) Covalent Bonding

Established procedures exist for covalently bonding biological materials, such as proteins, to cellulosic material. Published procedures include the use of chemical reagents which modify the polymer unit to form reactive groups which covalently bind to typical protein groups such as, for example, free amino groups.

Commonly used chemical reagents include:
cyanogen bromide
tosyl chloride
titanium complexes
carbodiimide
cyanuric chloride
oxirane
periodate.

(b) Non-Covalent Adsorption

Biological molecules, for example, sheep serum proteins, ribonucleases and immunoglobulins, have been found to bind very efficiently to cellulose nitrate. Simple addition of an aqueous protein solution at room temperature or lower has resulted in bound protein which could not easily be removed by washing with water, buffer solutions or detergents.

For example, incubation of a cellulose nitrate-coated grating for 2 hours at room temperature in 10 mgml$^{-1}$ bovine $\gamma$-globulin, 50 mM NaHCO$_3$, pH 9, resulted in extensive coverage of the diffraction grating with the protein. Various treatments, such as, for example, with mild detergent (5% Tween 20), buffer (50 mM NaHCO$_3$), n-heptane, and pH cycling between pH 2 and 10.6 did not affect the binding of the protein. Stronger detergent treatment (e.g. 2% SDS) has been found to damage the cellulose nitrate film.

(c) Reactive Polymer Entrapment

This procedure separates the two important functions of the diffraction grating layer
adhesion and conformation to the grating surface
reactivity towards protein or other biological material or binding partner
and meets each requirement with a separate polymer.

A monomeric material is allowed to diffuse into the polymer affixed to the diffraction gratinq. The monomer is then polymerized to give a network of the second polymer entangled in the first, affixed polymer. The second polymer is chosen to have chemical groups that are reactive towards protein or other biological molecules.

Thus, for example, diffraction gratings coated with cellulose nitrate according to the procedure described herein are incubated with 1% aqueous glutaraldehyde monomer solution pH 5.5 for 30 minutes at room temperature. The pH is then adjusted to 10, and the diffraction gratings left for 30 minutes to allow polymerisation of the glutaraldehyde. Polymerisation may be monitored by optical absorbance measurements at 235 nm. Such techniques have been previously described, see for example, U.S. Pat. No. 4,001,583. Free reactive carbonyl groups in the polyglutaraldehyde are thus exposed at the surface of the polymer layer.

Treatment of these diffraction gratings with protein solutions, e.g. 5 mgml$^{-1}$ bovine $\gamma$-globulin or 5 mgml$^{-1}$ ribonuclease, at 4° C. overnight in 50 mM NaHCO$_3$ pH 9, results in strong binding between the protein and the polyglutaraldehyde, believed to be the result of covalent bonding between the polyglutaraldehyde carbonyl groups and the amino groups of the proteins.

I claim:

1. A method of applying a uniform, thin polymer film to the surface of a metallized diffraction grating which comprises the steps of:
   (i) inserting the metallized diffraction grating into a bath containing a casting liquid,
   (ii) forming a thin film of a desired polymer over the surface of the casting liquid, and
   (iii) either raising the diffraction grating through the casting liquid to engage the film of polymer on the surface of the liquid or allowing the casting liquid to drain out of the bath so that the polymer film on the surface of the liquid drops as the liquid level drops until it engages and spreads over the surface of the diffraction grating, in either case the diffraction grating being located at a small angle to the horizontal to facilitate draining of the casting liquid from the surface of the diffraction grating.

2. The method of claim 1 wherein the thin polymer film is 5 to 100 nm thick.

3. The method of claim 2 wherein the casting solution is water and the polymer is cellulose nitrate.

4. The method of claim 3 wherein the thin film of polymer is formed by dropping a solution of cellulose nitrate in amyl acetate onto the water surface.

5. The method of claim 4 additionally comprising adsorbing on or binding to the thin polymer film either directly or indirectly, a specific binding partner for a ligand which is desired to be assayed.

6. A method of preparing an optical structure useful for the detection of a ligand in a spectrophotometric assay technique, said optical structure having a surface relief profile or being capable of supporting surface plasmon resonance, which method comprises applying to the entire surface of the optical structure a uniform, thin layer of an organic polymer by means of a solvent casting technique and adsorbing on or binding to the thin layer of organic polymer, either directly or indirectly, a specific binding partner for the ligand.

7. The method of claim 6 wherein the optical structure is a metallized diffraction grating.

8. The method of claim 7 wherein the thin layer of organic polymer is 5 to 100 nm thick.

9. The method of claim 8 wherein the metallized diffraction grating is adapted to support surface plasmon resonance of a ligand/specific binding partner complex formed thereon.

10. The method of claim 9 wherein the thin layer of organic polymer is activated prior to contact with the specific binding partner to facilitate binding thereof.

11. The method of claim 10 wherein the specific binding partner is applied to at least one discrete region of the thin layer of organic polymer to form at least one test region and a non-binding protein is applied to at least one other discrete region of the thin layer of organic polymer to form at least one reference region.

12. The method of claim 11 wherein the metallized diffraction grating has a surface comprising a thin film of silver less than 500 nm thick.

13. The method of claim 12 wherein the specific binding partner is an antigen or antibody.

14. The method of claim 13 wherein the organic polymer is cellulose nitrate.

15. An optical biosensor useful for the detection of a ligand in a spectrophotometric assay technique which comprises an optical structure having a surface relief profile coated over its entire surface with a uniform, thin layer of an organic polymer of 5 to 100 nm thick to which is bound or adsorbed, directly or indirectly, a specific binding partner for the ligand.

16. The optical biosensor of claim 16 wherein the optical structure is a metallized diffraction grating.

17. The optical biosensor of claim 16 wherein the metallized diffraction grating has a surface comprising a thin film of silver less than 500 nm thick.

18. In a method of detecting a ligand in a sample utilizing a spectrophotometric assay technique which comprises contacting the sample with an optical biosensor and measuring the change in optical characteristics of the optical biosensor caused by formation of a ligand/specific binding partner complex thereon, the improvement wherein the optical biosensor comprises an optical structure having a surface relief profile coated over its entire surface with a uniform, thin layer of an organic polymer of 5 to 100 nm thick to which is bound or adsorbed, directly or indirectly, the specific binding partner for the ligand.

19. The method of claim 18 wherein the optical structure is a metallized diffraction grating.

20. The method of claim 19 wherein the metallized diffraction grating has a surface comprising a thin film of silver less than 50 nm thick.

* * * * *